(12) United States Patent
Florent et al.

(10) Patent No.: US 9,700,209 B2
(45) Date of Patent: Jul. 11, 2017

(54) MEDICAL IMAGING DEVICE FOR PROVIDING AN IMAGE REPRESENTATION SUPPORTING IN POSITIONING AN INTERVENTION DEVICE

(75) Inventors: Raoul Florent, Ville D'Avray (FR); Bart Pierre Antoine Jozef Hoornaert, Arendonk (BE); Herman Stegehuis, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 558 days.

(21) Appl. No.: 14/003,486

(22) PCT Filed: Mar. 5, 2012

(86) PCT No.: PCT/IB2012/051021
§ 371 (c)(1),
(2), (4) Date: Sep. 6, 2013

(87) PCT Pub. No.: WO2012/123850
PCT Pub. Date: Sep. 20, 2012

(65) Prior Publication Data
US 2013/0343631 A1    Dec. 26, 2013

(30) Foreign Application Priority Data
Mar. 15, 2011  (EP) .................................. 11305285

(51) Int. Cl.
*G06K 9/00*  (2006.01)
*A61B 5/00*  (2006.01)
(Continued)

(52) U.S. Cl.
CPC .............. *A61B 5/0037* (2013.01); *A61B 6/06* (2013.01); *A61B 6/12* (2013.01); *A61B 6/487* (2013.01);
(Continued)

(58) Field of Classification Search
USPC .................................................. 382/128–134
See application file for complete search history.

(56) References Cited

U.S. PATENT DOCUMENTS 5,253,169 A    10/1993  Corby, Jr.
5,282,254 A *   1/1994  Chiu et al. .................... 382/132
(Continued)

FOREIGN PATENT DOCUMENTS

| DE | 102009015830 | 10/2010 |
| WO | WO2010041201 | 4/2010 |
| WO | WO2011039673 | 4/2011 |

*Primary Examiner* — Alex Liew (57) ABSTRACT

A medical imaging device and a method for providing an image representation supporting positioning of an intervention device such as a wire tip (4) in a region of interest during an intervention is proposed. Therein, the following process steps are to be performed: (S1) acquiring a pre-live anatomy image (1) including a region of interest; (S2) acquiring a live anatomy image using a live image acquisition device comprising an adjustable collimator device; (S3) identifying a location (5) of the intervention device (4) within the live anatomy image; (S4) adjusting settings of the collimator device based on the identified location of the intervention device for subsequently acquiring a further live anatomy image representing the region of interest using the live image acquisition device with the collimator device being in the adjusted settings; and providing (S5) the image representation by merging information from the live anatomy image into the pre-live anatomy image. Thereby, the intervention device may be continuously tracked and the collimator device may restrict a field of view to a location of the intervention device thereby significantly reducing an applied X-ray dose. Background anatomical information may be introduced into the final image representation using the pre-live anatomy image possibly having a higher image contrast than the live anatomy images.

16 Claims, 2 Drawing Sheets

(51) Int. Cl.
- *A61B 6/06* (2006.01)
- *A61B 6/12* (2006.01)
- *A61B 90/00* (2016.01)
- *A61B 6/00* (2006.01)

(52) U.S. Cl.
CPC ............ *A61B 6/5229* (2013.01); *A61B 90/37* (2016.02); *A61B 6/4441* (2013.01); *A61B 6/481* (2013.01); *A61B 6/503* (2013.01); *A61B 6/504* (2013.01); *A61B 6/542* (2013.01)

(56) References Cited

U.S. PATENT DOCUMENTS

| | | | |
|---|---|---|---|
| 6,359,956 B1* | 3/2002 | Hsieh et al. ................... 378/15 |
| 6,470,207 B1 | 10/2002 | Simon et al. |
| 7,340,033 B2* | 3/2008 | Mollus et al. ................. 378/62 |
| 2003/0091222 A1* | 5/2003 | Young et al. ................ 382/132 |
| 2003/0215122 A1* | 11/2003 | Tanaka ......................... 382/128 |
| 2004/0013293 A1* | 1/2004 | Klingenbeck-Regn ....... 382/131 |
| 2005/0053267 A1* | 3/2005 | Mostafavi ..................... 382/128 |
| 2006/0153468 A1 | 7/2006 | Solf |
| 2006/0182326 A1* | 8/2006 | Schildkraut et al. ......... 382/132 |
| 2006/0291712 A1* | 12/2006 | Popescu et al. ............... 382/134 |
| 2007/0183569 A1 | 8/2007 | Boese et al. |
| 2008/0025586 A1* | 1/2008 | Baumgart et al. ............ 382/128 |
| 2008/0031413 A1* | 2/2008 | Bouvier et al. ................. 378/63 |
| 2008/0031505 A1* | 2/2008 | Barski et al. ................. 382/132 |
| 2008/0118115 A1 | 5/2008 | Williamson |
| 2008/0137934 A1* | 6/2008 | Sakaguchi et al. ........... 382/132 |
| 2008/0187205 A1* | 8/2008 | Shiozawa et al. ............ 382/132 |
| 2009/0141854 A1* | 6/2009 | Hirokawa et al. ................ 378/4 |
| 2009/0147919 A1* | 6/2009 | Goto et al. ...................... 378/86 |
| 2009/0245466 A1* | 10/2009 | Wu .............................. 378/98.12 |
| 2010/0074505 A1* | 3/2010 | Oogami ........................ 382/132 |
| 2010/0174120 A1 | 7/2010 | Harmer et al. |
| 2010/0183215 A1* | 7/2010 | Sakai et al. ................... 382/132 |
| 2011/0096970 A1* | 4/2011 | Vija .............................. 382/131 |
| 2011/0293164 A1* | 12/2011 | Sato et al. .................... 382/132 |
| 2011/0317895 A1* | 12/2011 | Poludniowski et al. ...... 382/131 |
| 2013/0308844 A1* | 11/2013 | Florent et al. ................ 382/130 |
| 2013/0343631 A1* | 12/2013 | Florent et al. ................ 382/132 |

\* cited by examiner

Fig. 2

MEDICAL IMAGING DEVICE FOR PROVIDING AN IMAGE REPRESENTATION SUPPORTING IN POSITIONING AN INTERVENTION DEVICE

CROSS-REFERENCE TO PRIOR APPLICATIONS

This application is the U.S. National Phase application under 35 U.S.C. §371 of International Application Serial No. PCT/IB2012/051021, filed on Mar. 5, 2012, which claims the benefit of European Application Serial No. 11305285.6, filed on Mar. 15, 2011. These applications are hereby incorporated by reference herein.

FIELD OF THE INVENTION

The present invention relates to a medical imaging device which may be used for providing an image representation supporting in positioning of an intervention device in a region of interest during a medical intervention procedure. Furthermore, the present invention relates to a medical imaging system, a medical imaging method, a computer program and a computer-readable medium, all of which are adapted for providing an image representation which may be used in supporting for example a surgeon during positioning of a medical intervention device.

BACKGROUND OF THE INVENTION

During medical intervention procedures one or more intervention devices may have to be accurately positioned within a region of interest within a patient. For example e.g. during a cardiac catheterization a wire tip may have to be positioned at a precise location within a vessel system. In order to help a physician in such positioning, medical imaging devices are typically provided for displaying an image representation from which the physician may derive information about both the patient's anatomy within a region of interest and the current position of the intervention device.

Conventionally, X-ray imaging devices are used to provide a fluoroscopy image or a sequence of fluoroscopy images during the intervention procedure. In the fluoroscopy image(s), the physician may observe the actual position of the intervention device as such intervention device typically comprises X-ray opaque portions.

The acquisition of a plurality of X-ray fluoroscopy images implies that the patient is subject to an essential X-ray exposure. However, an X-ray dose transmitted through the patient's body should be as low as possible. In order to reduce the X-ray exposure, U.S. Pat. No. 7,340,033 B2 proposes to use an X-ray image acquisition device comprising an adjustable collimator, to determine a region of interest from an acquired X-ray picture and to adjust the collimator thereon. Therein, the region of interest can be chosen to be large enough for the irradiation field to cover all those positions of an organ of interest that occur as a result of heartbeat and/or respiration.

Furthermore, X-ray fluoroscopy images may suffer from a poor contrast such that the patient's anatomy may be difficult to observe in such fluoroscopy images and it may be difficult to determine where the intervention device is positioned relative to the patient's anatomy.

SUMMARY OF THE INVENTION

There may be a need for a medical imaging device which may at least partly overcome the above-mentioned deficiencies. Particularly, there may be a need for a medical imaging device which enables reducing an X-ray exposure to the patient during positioning of an intervention device in a region of interest during a medical intervention procedure. Furthermore, there may be a need for a medical imaging device providing a detailed image representation indicating a position of the intervention device within the patient's anatomy. Furthermore, there may be a need for a corresponding medical imaging system, a medical imaging method, a computer program and a computer-readable medium adapted for providing such advantageous image representation.

Such needs may be met by the subject-matter of the independent claims. Advantageous embodiments are defined in the dependent claims.

According to a first aspect of the present invention, a medical imaging device for providing an image representation supporting in positioning an intervention device in a region of interest during an intervention procedure is proposed. The medical imaging device is adapted for performing the following steps:

(i) acquiring a pre-live anatomy image including the region of interest;

(ii) acquiring a live anatomy image including the region of interest using a live image acquisition device comprising an adjustable collimator device with the collimator device being in previously set settings;

(iii) identifying a location of the intervention device within the live anatomy image;

(iv) adjusting settings of the collimator device based on the identified location of the intervention device for subsequently acquiring a further live anatomy image including the region of interest using the live image acquisition device with the collimator device being in the adjusted settings;

(v) providing the image representation by merging information from the live anatomy image into the pre-live anatomy image.

It may be noted that the above-mentioned steps may be performed in the indicated order. Particularly, the one or more pre-live anatomy images and live anatomy images may represent a same region of interest within the patient wherein the pre-live anatomy image(s) may be acquired prior to starting the actual intervention procedure whereas the live anatomy images are acquired during the intervention procedure. For example, the pre-live anatomy image(s) may be angiogram images whereas the live anatomy images may be fluoroscopy images. Particularly, a plurality of live anatomy images may be acquired wherein the above-mentioned steps (ii) to (v) are continuously repeated such that a sequence of image representations may be provided by merging information from each of the plurality of live anatomy images with a corresponding pre-live anatomy image.

A second aspect of the present invention relates to a medical imaging system comprising a pre-live image acquisition device for acquiring high contrast images; a live image acquisition device for acquiring low contrast images, the live image acquisition device comprising an adjustable collimator device; the above-mentioned medical imaging device; and a display for displaying the image representation provided by the medical imaging device.

A third aspect of the present invention relates to a medical imaging method comprising method steps as defined above with respect to the first aspect of the invention.

A fourth aspect of the invention relates to a computer program adapted for performing such method when executed on a computing device.

A fifth aspect of the invention relates to a computer-readable medium such as a CD-ROM is presented wherein the computer-readable medium has a computer program as described in the preceding section stored thereon. However, the computer program may also be presented over a network and may be downloaded into the working memory of a data processor from such network. Accordingly, the computer-readable medium may be a medium for making a computer program available for downloading to a computer-readable medium comprising stored thereon such computer program.

A gist of the present invention may be seen as based on the following ideas:

The proposed medical imaging device combines two main features for providing an informative image representation indicating the location of an intervention device within a region of interest and thereby helping a surgeon to correctly position the intervention device:

(a) the location of the intervention device may be continuously tracked and an X-ray image acquiring mode may be adapted depending on the current location of the intervention device. Therein, live anatomy images are acquired and a location of the intervention device within a respective live image is determined. Based on such determined location of the intervention device, the settings of a collimator device such as an X-ray absorbing shutter or an X-ray attenuating wedge arrangement may be adjusted. In other words, for example the position of a shutter or of wedges of the collimator device may be set such that an acquisition of a subsequent live anatomy image is restricted to a partial area of the region of interest adjacent to the determined location of the intervention device. In accordance with such restriction, only a partial area of the region of interest is subjected to X-rays for acquiring the subsequent live images. Accordingly, an overall X-ray dose transmitted through the patient may be significantly reduced.

(b) However, it has been realized that the continuous adjusting of collimator settings, i.e. the continuous repositioning of shutters or wedges for example, may result in a troublesome visual impression of the acquired live images. Therefore, it is proposed to additionally acquire one or more pre-live anatomy images of the region of interest and to merge a respective pre-live anatomy image with a corresponding live anatomy image to finally provide an image representation in which details of the surrounding anatomy may be represented mainly based on the pre-live anatomy image whereas details on the current position of the intervention device may be represented based on the current live image.

Therein, it may be beneficial that the pre-live anatomy image(s) may be acquired with a higher image contrast than in the live anatomy images. For example, the pre-live anatomy image may be an angiography image which is acquired with a relatively high X-ray dose and while an X-ray absorbing contrast medium is present within the region of interest. The live anatomy images may be acquired as fluoroscopy images during the intervention procedure without the presence of contrast medium. Therein, an overall X-ray dose may be significantly reduced due to continuous tracking of the current location of the intervention device and adjusting settings of the collimator device such that the live images are acquired only in a restricted area adjacent to such current location of the intervention device.

A final image representation to be presented e.g. to a surgeon for supporting in positioning of the intervention device in the region of interest may then be provided by merging a live anatomy image and a pre-live anatomy image such that in the provided image representation a region adjacent to the location of the identified intervention device is represented mainly based on the live anatomy image whereas a region distant to the location of the identified intervention device is represented mainly based on the pre-live anatomy image. In other words, the location of the intervention device is visualized based mainly on the current live anatomy image whereas the information about the patient's anatomy within the region of interest is provided based mainly on the previously acquired pre-live anatomy image usually having a higher contrast than the live images.

With such technique, an overall radiation dose may be reduced by limiting the live image acquisition to the actual area surrounding the intervention device while restoring the occluded anatomy background with pre-live, possibly richer content previously acquired and possibly acquired in diagnostic conditions.

It has to be noted that features and advantages of embodiments of the invention are described herein with reference to different subject-matters. In particular, some embodiments are described with respect to method type features whereas other embodiments are described with respect to device type features. However, a person skilled in the art will gather from the above and the following description that, unless otherwise notified, in addition to any combination of features belonging to one type of subject-matter also any combination of features relating to different subject-matters is considered to be disclosed with this application. Particularly, features can be combined providing synergy effects that are more than the simple sum of the features.

BRIEF DESCRIPTION OF THE DRAWINGS

Features and embodiments defined above and further features and advantages of the present invention can also be derived from the examples of embodiments to be described hereinafter and are explained with reference to embodiments, but to which the invention is not limited. The invention will be described in more detail hereinafter with reference to the drawings.

The figures are only schematically and not to scale.

DETAILED DESCRIPTION OF EMBODIMENTS

Figure 1:
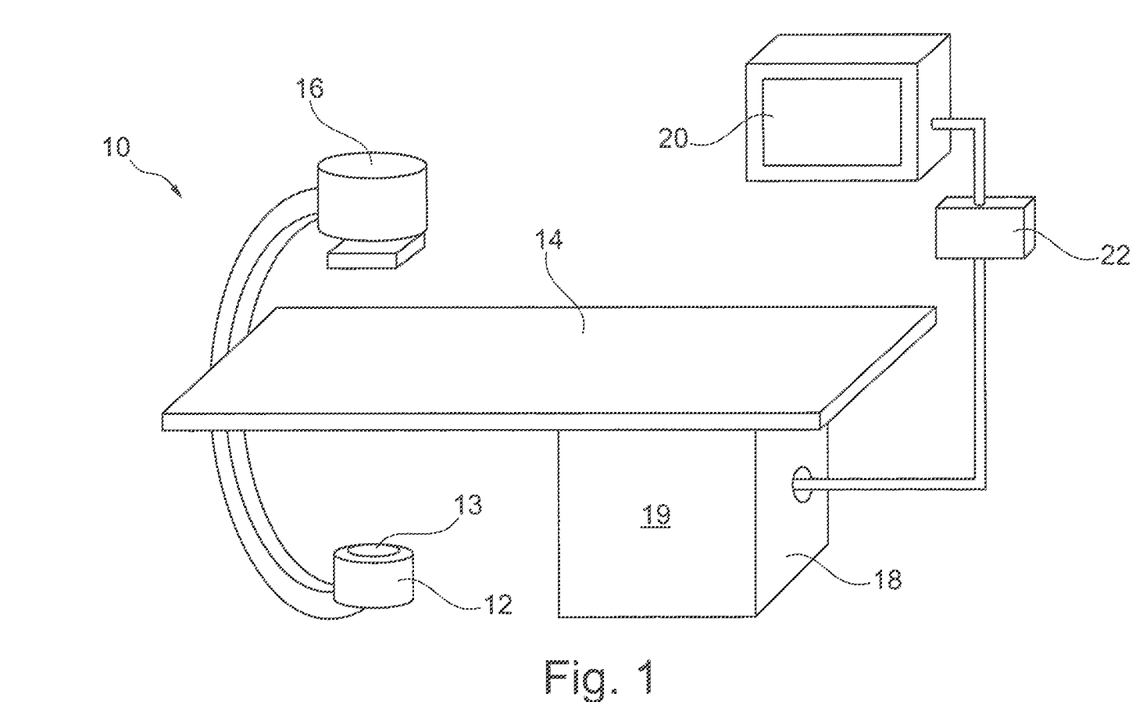
FIG. 1 shows an X-ray imaging system which may use a medical imaging device or a medical imaging method according to an embodiment of the present invention.

FIG. 1 schematically shows an X-ray medical imaging system 10 which may be used during an intervention procedure to provide an image representation thereby supporting a surgeon in positioning an intervention device within a patient in accordance with an embodiment of the present invention.

The imaging system 10 comprises an X-ray image acquisition device with an X-ray source 12 provided to generate X-ray radiation. The X-ray source 12 comprises a collimator 13 including shutters and wedges (not shown) in order to collimate the X-radiation onto a region of interest. A table 14 is provided to receive a patient to be examined. Furthermore, an X-ray image detection module 16 is located opposite to the X-ray source 12. During an imaging procedure, the patient is located on the table 14, i.e. between the X-ray source 12 and the detection module 16. X-rays are emitted by the X-ray source 12 and transmitted through the patient before being detected by the detection module 16.

The detection module 16 is sending data to a data processing unit 18 which is connected to both the X-ray source 12 and the detection module 16. The data processing unit 18 includes a processor and a computer-readable memory carrying software for controlling the processor to acquire anatomy images and process the same in accordance with the processing steps outlined above and hereinafter. Thus, the data processing unit 18 comprises data interfaces to acquire pre-live and live anatomy images and is adapted to detect the location of an intervention device in a live anatomy image in order to thereupon control the collimator 13 of the X-ray source 12 to focus onto such location. Furthermore, the data processing unit 18 is adapted for merging of pre-live and live anatomy images. Accordingly, the data processing unit 18 may serve as a medical imaging device 19 according to an embodiment of the present invention.

Furthermore, the data processing unit 18 is connected to a display device 20 for displaying information to a person operating the X-ray imaging system, i.e. a clinician such as a cardiologist or a cardiac surgeon. For example, image representations indicating a current location of an intervention device within the patient may be displayed on the display device 20. The display device may also be used to display two images such as e.g. both the image representation indicating a current location of an intervention device as provided by the medical imaging device 19 as well as a live image which has not been further processed and which provides a good live information on the operation site. Furthermore, an interface unit 22 is provided in order to enable an information input by the operating person.

It is noted that the example shown in FIG. 1 is of a so-called C-type X-ray image acquisition device. Of course, the invention may also relate to other types of medical imaging systems.

In the following, an operation mode and process steps to be performed by the medical imaging system in accordance with an embodiment of the present invention shall be described with reference to the chart shown in FIG. 2.

In order to perform a medical imaging method in accordance with embodiments of the present invention, two data inputs are performed as follows.

First, a pre-live anatomy image 1 or a sequence of pre-live anatomy images is acquired (step (S1)). Therein, a pre-live anatomy image represents a region of interest within a patient. For example, a cardiac vessel region is represented. The pre-live anatomy image is typically acquired prior to or in the periphery of an intervention procedure, i.e. at pre-interventional or peri-interventional phases, in which an intervention device such as e.g. a guide-wire is to be positioned within the region of interest. Typically, the pre-live anatomy image can be an angiography image. Preferably, a sequence of angiographic images forming a pre-live anatomy image sequence is acquired. In general this sequence does not contain any intervention devices that will be manoeuvred during the actual intervention procedure such as e.g. a wire tip, but it may contain devices that will not be manoeuvred during the intervention procedure such as e.g. a catheter injection tip.

Generally, the pre-live anatomy image or pre-live anatomy image sequence features the same region of interest as subsequently featured during the intervention procedure with the live anatomy images. However, in the pre-live anatomy image(s) features may possibly be enhanced by an increased contrast as such images may be acquired with a higher X-ray dose than used in subsequent live anatomy image acquisition. Furthermore, during acquisition of the pre-live anatomy image(s) a contrast medium may be present within the region of interest. For example, in a preceding step, a contrast medium may be injected into the patient's vessels. Thereby, exposure conditions may be enhanced thereby enabling better image contrast compared to subsequently acquired live anatomy image acquisition.

The pre-live anatomy image(s) may be acquired with the same imaging system 10 as used subsequently for acquiring the live anatomy images during the intervention procedure. Alternatively a DRR (digitally reconstructed radiograph) sequence or a projection sequence from a 3D volume acquired on the same or another X-ray medical imaging system or even from another modality such as CT (computer tomography) or MR (magnetic resonance) may be used for acquiring the pre-live anatomy image(s). In case of MR the reconstruction of an "X-ray-like pre-live image sequence" may require some extra computations. Alternatively, an "MR-like" background may also be sufficient for guidance during an X-ray intervention. In case of a DRR, it may not be necessary to calculate a full DRR as background image, but only a vessel or organ that is relevant as a road map to guide the intervention device. The pre-live anatomy image may be 2D, 3D, 4D or even more dimensional. Typically in Electro-Physiology (EP) procedures such as Atrial Fibrillation (AF) procedures, one often resorts to a pre-live segmentation of part of the heart in a CT volume, typically the left atrium, which might be used as a source for pre-live anatomy image generation. The pre-live anatomy image can therefore be constituted from segmentation or modelling data, as opposed to direct acquisition data. In AF, typically the segmented left atrium from a CT volume, can be projected and variously rendered onto a 2D plane compatible with the live image plane. The term image in the expression "pre-live anatomy image" should therefore be understood in a broad way, as a data source representing the anatomy and compatible with a subsequent merging with the live images.

Another typical intervention is Percutaneous aortic Valve Replacement (PVR). In this kind of procedures, the aortic cross and aortic root are typically segmented from a CT volume. This segmentation can also serve to produce a pre-live anatomy image.

As a second data input, a first live anatomy image 2 of the region of interest is acquired (step (S2)). For this image acquisition, an image acquisition device comprising an adjustable collimator device is used. Typically, an X-ray fluoroscopy imaging device is used, such fluoroscopy imaging device comprising a collimator device which includes at least one of an X-ray absorbing shutter device and an X-ray attenuating wedge device. However, the collimator device may also include other types of controllable X-ray absorbing or X-ray attenuating devices which may be controlled such that their X-ray absorbing or X-ray attenuating properties may be locally varied. Herein, X-ray absorbing may mean that no X-rays are transmitted through the X-ray absorbing devices; X-ray attenuating may mean that X-rays are partially transmitted through the X-ray absorbing devices. Using the example of a collimator having a shutter and/or wedge device, by introducing the shutter and/or wedge into an X-ray beam emitted by the X-ray source, such X-ray beam may be collimated, i.e. its lateral dimensions may be restricted such that the imaging area from which the live anatomy image is acquired may be limited. While for acquiring the first live anatomy image, the collimator device may be in its fully opened state such that the entire area of the region of interest is imaged, subsequent live anatomy images may be acquired with a restricted setting of the collimator device such that only a partial area of the region of interest adjacent to a previously identified location of an intervention device is imaged. The live anatomy image(s) is typically acquired with the intervention device being present within the region of interest. For example, in cardiac catheterization, this intervention device can be a catheter injection tip 3 and a wire tip 4. In AF procedures, the intervention device may be in fact multiple, and constituted by a certain number of electrodes and catheters. In PVR interventions, the device is typically constituted by the artificial valve to be deployed. However, the device can also include a monitoring ultrasound probe. Generally speaking, the term device can therefore refer to several separated entities which are manoeuvred during the intervention, and within the region of interest. These entities might be prosthesis, delivery tools, measuring tools, etc.

Subsequent to acquiring a first live anatomy image, a location of the intervention device(s) of interest such as of the wire tip 3 and/or the injection tip 4 is identified within the live anatomy image (step (S3)). In other words, the intervention device(s) may be tracked within a sequence of live anatomy images. The location of the intervention device(s) may be determined based on analyzing location information, shape information and/or radiometric content comprised in the first live anatomy image. For identifying the current location of the intervention device(s), conventional segmentation tools may be used. Such segmentation tools preferably allow real-time identification of the intervention device(s). However, the determination of the device (s) location might also be determined by non-imaging material, such as through active localiser, typically Electro-Magnetic trackers (EM trackers). When used, those trackers are directly mounted on the device(s) of interest.

The term location should be understood in a broad sense. It might refer to the location of a precise point of the device, but it also might refer to several points on the device, or even to all the pixels of the live image corresponding to the device. When several devices are involved, each individual device might be located, or conversely, a global representative location of all these devices might be sufficient, typically a barycentre location.

Furthermore, in identifying the location of the intervention device(s), a prediction on a future location of the intervention device(s) based on current location parameters or motion parameters may be involved. For this purpose, a trajectory of the intervention device(s) may be analyzed and a probability map of their predicted future locations may be built. This may allow anticipating the devices movements such that it may be possible to predict the future location 5 of the intervention device(s). Usual temporal filtering methods may be used to generate such predictions.

After having identified the current location of an intervention device and, optionally, a predicted location of the intervention device, settings of the collimator device comprised in the live image acquisition device are adjusted based on such identified location (step S4). When the collimator device comprises at least one of a shutter 7 and a wedge 6 device for locally reducing an X-radiation flow from the X-ray source through the patient towards the X-ray detector, such settings of the collimator device may indicate a positioning of the shutter 7 or wedge 6 device. In other words, by adjusting the settings of the collimator device, continuous shuttering or wedging, i.e. repositioning of the shutter 7 or wedge 6, may be applied so as to keep the intervention device visible within a live anatomy image to be subsequently acquired while occluding out the field of view as much as possible.

Once, the predicted locations 5 of the intervention devices 3, 4 are known, it is possible to optimize a compromise between tight shuttering/wedging and a probability that in a subsequent live anatomy image the intervention devices will remain within a non-occluded, that is non-collimated, area. For example, a safety margin may be defined around the predicted locations 5 and the setting of the collimator device may be adjusted such that wedges 6 and shutters 7 of the collimator device are repositioned in order to keep the non-occluded areas 8 as small as possible. At the same time, the wedges 6 and shutters 7 may be positioned such that a risk that the intervention devices 3, 4 move out of the non-occluded areas before a next live anatomy image is acquired is minimized. In case a probability map of predicted locations of the intervention devices 3, 4 has been prepared, safety margins to be considered for the shutter/wedge placement may be directly related to iso-contours of such probability maps.

In case it is detected that in a subsequent image acquisition the intervention device moved out of the collimated, non-occluded area 8, the collimator may be completely opened such that the intervention device may be found within the entire live image and the shutter or wedge may then be repositioned.

After having adjusted the settings of the collimator device, the entire process including steps (S2) to (S4) may be repeated such that a subsequent live anatomy image of a non-occluded area 8 may be acquired with the collimator device of the live image acquisition device being in the adjusted settings. In other words, predicted locations of the intervention devices 3, 4 which are acquired based on a previous live anatomy image at a point in time (t−1) may be used to accurately and efficiently place the shutters/wedges of the collimator device for subsequent live anatomy image acquisition at a point in time (t).

Information comprised in the live anatomy image may then be merged into the pre-live anatomy image in order to provide an image representation 9 in which both the information about the current position of the intervention devices 3, 4 as well as the information about the background anatomy in the region of interest are clearly visible (step (S5)).

Merging of the two anatomy images may require complex computations which however are generally known as so-called inverse-road mapping techniques as for example described in International Publication No. WO2011039673. Basically, a spatio-temporal transform linking the pre-live anatomy image(s) and the live anatomy image(s) may be determined. Generally, such spatio-temporal transform may be acquired depending on motion analysis of an organ comprised in the region of interest, and/or a geometry. For example, the organ may be a patient's heart and the motion analysis may include a breathing and cardiac phase analysis. The geometry taken into account for generating the spatio-temporal transform may relate to a position of the patient table, the X-ray source and/or the X-ray detector. Likewise, the involvement of the tracking of the intervention devices in this process may be more or less pronounced. Optionally, active tracking methods using for example electromagnetic sensors may also be applied.

Once the spatio-temporal transform is known, it may be applied to a region adjacent to the tracked intervention devices that are not present in the pre-live anatomy image(s), i.e. typically those intervention devices which are maneuverer in the live anatomy images, e.g. the wire tip 4. Thereby, a portion of the second live anatomy image in a region adjacent to the location of the identified intervention device 4 is represented in the final image representation. In other words, in the final image representation provided by merging the live anatomy image and the pre-live anatomy image, a region adjacent to the location of the identified intervention device 4 is represented mainly based on the live anatomy image. A region further distant to the location of the identified intervention device 4 is represented mainly based on the pre-live anatomy image. Typically, a transparency level may be determined below which only the background anatomy from the pre-live anatomy image is shown and above which the intervention device shown in the live anatomy image and the anatomy background shown in the pre-live anatomy image are nicely blended together.

Alternatively, information about the identified location of the intervention device may be used in order to visualize a model of the intervention device or any location identifier at the corresponding position within the finally provided image representation.

While the process steps to be performed by the medical imaging device according to an embodiment of the present invention are described above with respect to a first and subsequent live anatomy image only, a plurality of live anatomy images may be acquired during the intervention procedure by continuously repeating the process steps of identifying the location of the intervention device, adjusting the settings of the collimator device and acquiring a subsequent live anatomy image using the adjusted collimator settings. By merging each of the live anatomy images with the pre-live anatomy image or a selected image out of a sequence of pre-live anatomy images, a sequence of image representations may be provided. In such sequence, the motion of the intervention device may be clearly represented as the intervention device is continuously tracked and the live anatomy images focused on the tracked intervention device are then superimposed to a respective pre-live anatomy image possibly having a higher image contrast than the live anatomy images due to the possible use of a higher X-ray dose and/or a contrast medium.

Figure 2:
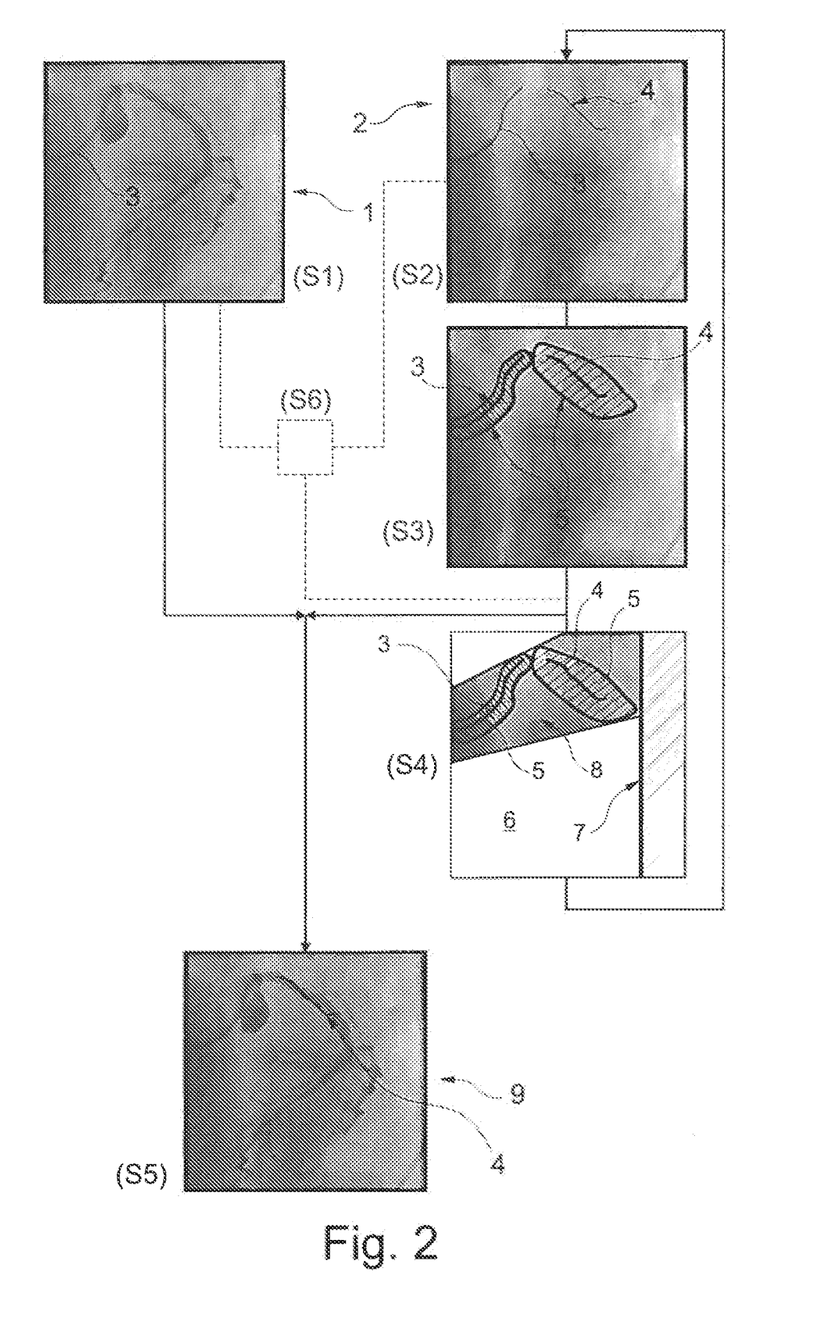
FIG. 2 shows a chart describing method steps performed by a medical imaging device according to an embodiment of the present invention.

As an option, the proposed medical imaging device may also include a device-based automatic exposure control (AEC), indicated in FIG. 2 as (S6). The AEC may be adapted to the proposed imaging method in accordance with embodiments of the present invention. This means that both a total image rendering as well as an intervention device detection and tracking process may be optimized through an appropriate control of radiation exposures. Several possibilities can be considered. For example, obvious real-time exclusion of collimated areas, i.e. areas shaded by wedging or shuttering, from a measuring field taken into account by the AEC may be performed. Additionally or alternatively, a fine adaptation of the AEC may be performed so that the total rendered scene, i.e. the background anatomy provided by the pre-live anatomy image together with image information on the intervention device provided by the live anatomy image, may be optimized from a visual perception point of view. Furthermore, the AEC may be adapted in real-time so as to reach a compromise between an optimal rendering of the resulting composite scene, i.e. background anatomy information plus intervention device information, and a detectability of the intervention devices. All such possible controls may be of course dynamic, i.e. continuously updated with real-time information coming from both the pre-live and live anatomy images 1, 2 and the intervention device tracking/prediction module.

Finally, important aspects and features of embodiments of the present invention shall be summarized in an alternative wording. Aspects of the invention rely on two main features:

a) On the one hand, it is proposed to track intervention devices of interest during a targeted intervention and to adapt a radiation limitation on an image basis to locations or predicted locations of those intervention devices. Such adaptation may be as tight as possible, optimizing both radiation reduction and a probability of keeping the intervention devices within a continuously adapted non-occluded field of view;

b) On the other hand, to suppress a troublesome visual impression undoubtedly created by continuously moving shutters or wedges of a collimator device, it is proposed to resort to a generalization of an inverse road mapping technique. Thereby, only surroundings of the intervention devices are taken from live anatomy images and are shown over pre-live non-tightly-shuttered background anatomy images, typically but not necessarily contrast-filled angiogram images.

In other words, device tracking is used to determine and predict locations of intervention devices of interest; image-level control is involved to apply dynamic tight collimation, concentrating radiation on an intervention focal point only that is around the tracked intervention devices; only live image data in a close vicinity of those tracked intervention devices are retained; they are projected and superimposed to a pre-live background anatomy image sequence which might constitute a richer background setting because it may be acquired with more doses and potentially with contrast medium.

With the proposed technique, a live radiation toll may be optimized to the visibility of the intervention devices only, while restoring an occluded background with pre-live anatomy image content, possibly richer in contrast information and possibly being acquired in diagnostic conditions.

The proposed invention may be used in a variety of X-ray intervention applications. In particular, it may be used in complex cardiac percutaneous catheterization procedures where a surgeon has to deal with both strong respiratory and cardiac motions. However, it may also be applied in many less demanding applications such as vascular or possibly neuro interventions.

Finally, it has to be noted that herein the word "comprising" does not exclude other elements or steps and that the indefinite article "a" or "an" does not exclude a plurality. Reference signs in the claims should not be construed as limiting the scope.

The invention claimed is:

1. A medical imaging device for providing an image representation supporting positioning of an intervention device in a region of interest during an intervention procedure, the medical imaging device comprising:
   (i) means for acquiring a pre-live anatomy image including the region of interest;
   (ii) means for acquiring a first live anatomy image including the region of interest using a live image acquisition device comprising an adjustable collimator device with the collimator device being in previously set settings;
   (iii) means for identifying or receiving a location of the jute device, within the first live anatomy image;
   (iv) means for adjusting settings of the collimator device based on the identified location of the intervention device for subsequently acquiring a further live anatomy image including the region of interest using the first live image acquisition device with the collimator device being in the adjusted settings;
   (v) means for acquiring a second live anatomy image including the region of interest using the collimator device with adjusted settings;

(vi) means for providing the image representation by merging information from the live anatomy image into the pre-live anatomy image.

2. The device of claim 1, further including:
(vii) means for merging the live anatomy image and the pre-live anatomy image such that in the provided image representation a region adjacent to the location of the identified intervention device is represented mainly based on the live anatomy image and a region distant to the location of the identified intervention device is represented mainly based on the pre-live anatomy image.

3. The device of claim 1, wherein functions (ii) to (vi) are continuously repeated for providing a sequential image representation.

4. The device of claim 3, further including:
means for identifying a location of the device within the second live anatomy image;
wherein the means for adjusting settings of the collimator based on the location of the interventional device in the second live anatomy image, adjusts the settings such that the acquiring of the second and third live anatomy images is restricted to a partial non-occluded area of the region of interest adjacent to the location of the identified intervention device.

5. The device of claim 1, wherein the means for acquiring the pre-live and live images include an X-ray imaging device, wherein the collimator device comprises at least one of an X-ray absorbing device and an X-ray attenuating device for locally reducing X-radiation flow and wherein the settings of the collimator device relate to a positioning of the at least one of the X-ray absorbing device and an X-ray attenuating device.

6. The device of claim 1, wherein, the identifying means further identifies a location of the intervention device includes predicting a future location of the intervention device based on current location parameters and motion parameters.

7. The device of claim 1, wherein the settings adjusting means includes at least one of a spatial and a temporal transformation of the pre-live anatomy image and the live anatomy image before the merging.

8. The device of claim 1, wherein the pre-live anatomy image acquiring means acquires the pre-live image with a higher image contrast than the live anatomy images.

9. The device of claim 1, wherein the pre-live image is an angiography image.

10. The device of claim 1, wherein the first and second live images are fluoroscopy images.

11. The device of claim 1, wherein the locating means locates the intervention device based on analyzing location information, shape information and radiometric content comprised in the live anatomy image.

12. A medical imaging device according to claim 1 wherein:
the pre-live image acquisition means is configured for acquiring high-contrast images;
the live image acquisition means is configured for acquiring a series of low-contrast images, the live image acquisition means comprising an adjustable collimator device;
a display configured to display the image representation provided by the image representation providing means.

13. A medical imaging method for providing an image representation supporting positioning of an intervention device in a region of interest during an intervention procedure, the medical imaging method including the following steps:
(i) from a pre-live image acquisition device, acquiring a pre-live anatomy image representing the region of interest;
(ii) from a live image acquisition device having an adjustable collimator device, acquiring a first live anatomy image representing the region of interest;
(iii) identifying a location of the intervention device within the first live image with the collimator device being in previously set setting;
(iv) adjusting the setting of the collimator device based on the identified location of the intervention device;
(v) subsequently acquiring a second live anatomy image representing the region of interest using the live image acquisition device with in the adjusted settings;
(vi) sequentially merging information from the first and second live anatomy images into the pre-live anatomy image to generate a sequence of image representations.

14. A non-transitory computer-readable medium having stored thereon a computer program which, when executed on a computing device, performs the method of claim 13.

15. A medical imaging device configured to display a sequence of image representations supporting positioning of an intervention device in a region of interest during an intervention procedure, the medical imaging device including:
a processor controlled by software carried in a computer-readable memory to:
(i) receive a pre-live anatomy image including the region of interest,
(ii) receive a sequence live anatomy images including the region of interest from a live image acquisition device including an adjustable collimator device,
(iii) receive an identification of a location of the intervention device in a first live anatomy image of the sequence of live anatomy images with the collimator device in a previous setting,
(iv) determine an adjustment to the setting of the collimator device based on the identified location of the intervention device,
(v) subsequently receive a further live anatomy image including the region of interest using the adjusted collimator setting,
(vi) sequentially merge information from the first and subsequent live anatomy images into the pre-live anatomy image to form the sequence of image representations, and
a display device configured to display the sequence of image representations.

16. The device of claim 15, wherein merging the information from the first and subsequent live images into the pre-live image includes operating on one of the pre-live and live images with a spatio-temporal transform.

* * * * *

UNITED STATES PATENT AND TRADEMARK OFFICE
CERTIFICATE OF CORRECTION

PATENT NO. : 9,700,209 B2
APPLICATION NO. : 14/003486
DATED : July 11, 2017
INVENTOR(S) : Raoul Florent et al.

It is certified that error appears in the above-identified patent and that said Letters Patent is hereby corrected as shown below:

In the Claims

Column 10, In Claim 1, Line 58, the word "jute" should be corrected to read --intervention--.

Signed and Sealed this
Seventh Day of November, 2023

Katherine Kelly Vidal
*Director of the United States Patent and Trademark Office*